(12) United States Patent
Ostroot et al.

(10) Patent No.: US 12,059,192 B2
(45) Date of Patent: *Aug. 13, 2024

(54) CLOSED IRRIGATED RADIOFREQUENCY BIPOLAR TINED ABLATION PROBE

(71) Applicant: Boston Scientific Scimed, Inc., Maple Grove, MN (US)

(72) Inventors: Timothy A. Ostroot, Cokato, MN (US); Hong Cao, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 94 days.

This patent is subject to a terminal disclaimer.

(21) Appl. No.: 17/838,012

(22) Filed: Jun. 10, 2022

(65) Prior Publication Data

US 2022/0296292 A1 Sep. 22, 2022

Related U.S. Application Data

(63) Continuation of application No. 16/695,622, filed on Nov. 26, 2019, now Pat. No. 11,382,682.

(Continued)

(51) Int. Cl.
*A61B 18/14* (2006.01)
*A61B 18/00* (2006.01)

(52) U.S. Cl.
CPC .... *A61B 18/14* (2013.01); *A61B 2018/00023* (2013.01); *A61B 2018/00577* (2013.01);

(Continued)

(58) Field of Classification Search
CPC ................ A61B 18/14; A61B 18/1482; A61B 2018/00023; A61B 2018/00577;

(Continued)

(56) References Cited

U.S. PATENT DOCUMENTS

| 4,823,812 A | 4/1989 | Eshel et al. |
| 5,348,554 A | 9/1994 | Imran et al. |

(Continued)

FOREIGN PATENT DOCUMENTS

| CA | 2870616 | 10/2013 |
| CN | 113194860 | 7/2021 |

(Continued)

OTHER PUBLICATIONS

"International Preliminary Report on Patentability," for PCT Application No. PCT/US2019/067155 mailed Jul. 1, 2021 (8 pages).

(Continued)

*Primary Examiner* — Michael F Peffley
(74) *Attorney, Agent, or Firm* — Pauly, DeVries Smith & Deffner LLC

(57) ABSTRACT

The disclosure relates to systems and methods for irrigated bipolar radiofrequency ablation. The system includes an ablation probe that includes an elongate inner electrode assembly and an elongate outer electrode assembly. An irrigation path for irrigation fluid flow is defined between the outer surface of the inner electrode assembly and the outer surface of the outer electrode assembly. The irrigation path enables cooling fluid to be circulated within the probe body, cooling the outer electrode during ablation.

20 Claims, 6 Drawing Sheets

Related U.S. Application Data

(60) Provisional application No. 62/772,421, filed on Nov. 28, 2018.

(52) U.S. Cl.
CPC .............. *A61B 2018/00791* (2013.01); *A61B 2018/1467* (2013.01); *A61B 2218/002* (2013.01)

(58) Field of Classification Search
CPC ........... A61B 2018/00791; A61B 2018/00821; A61B 2018/143; A61B 2018/1467; A61B 2018/1475; A61B 2218/002
See application file for complete search history.

(56) References Cited

U.S. PATENT DOCUMENTS

| | | | |
|---|---|---|---|
| 5,807,395 A | 9/1998 | Mulier et al. | |
| 5,810,804 A * | 9/1998 | Gough ............... | A61B 18/1482 606/41 |
| 6,030,379 A | 2/2000 | Panescu et al. | |
| 6,241,722 B1 | 6/2001 | Dobak et al. | |
| 6,379,378 B1 | 4/2002 | Werneth et al. | |
| 6,514,251 B1 | 2/2003 | Ni et al. | |
| 8,235,981 B2 | 8/2012 | Prakash et al. | |
| 8,279,604 B2 | 10/2012 | Jones et al. | |
| 9,820,814 B2 | 11/2017 | Turovskiy et al. | |
| 11,382,682 B2 | 7/2022 | Ostroot et al. | |
| 11,957,409 B2 | 4/2024 | Cao et al. | |
| 2002/0026188 A1 * | 2/2002 | Balbierz ............ | A61B 18/1206 606/41 |
| 2003/0014044 A1 | 1/2003 | Krishnan et al. | |
| 2004/0116921 A1 * | 6/2004 | Sherman ............ | A61B 17/2202 606/41 |
| 2004/0176761 A1 * | 9/2004 | Desinger ............ | A61B 18/1492 606/50 |
| 2004/0220562 A1 * | 11/2004 | Garabedian ........ | A61B 18/1477 606/41 |
| 2006/0122593 A1 * | 6/2006 | Jun .................... | A61B 18/1477 606/41 |
| 2006/0178666 A1 * | 8/2006 | Cosman ............... | A61B 18/148 606/41 |
| 2008/0147060 A1 | 6/2008 | Choi | |
| 2009/0295674 A1 | 12/2009 | Bonn | |
| 2011/0066144 A1 | 3/2011 | Bonn et al. | |
| 2011/0264084 A1 | 10/2011 | Reid | |
| 2013/0281851 A1 | 10/2013 | Carr | |
| 2015/0272669 A1 | 10/2015 | Brucker et al. | |
| 2016/0095657 A1 | 4/2016 | Brannan | |
| 2019/0015152 A1 | 1/2019 | Howard et al. | |
| 2020/0163709 A1 | 5/2020 | Ostroot et al. | |
| 2020/0197089 A1 | 6/2020 | Cao et al. | |

FOREIGN PATENT DOCUMENTS

| | | |
|---|---|---|
| EP | 3860488 | 8/2021 |
| EP | 3860488 | 5/2024 |
| WO | 2020132058 | 6/2020 |

OTHER PUBLICATIONS

"International Search Report and Written Opinion," for PCT Application No. PCT/US2019/067155 mailed Mar. 13, 2020 (13 pages).

"Non-Final Office Action," for U.S. Appl. No. 16/717,113 mailed May 11, 2022 (30 pages).

"Notice of Allowance," for U.S. Appl. No. 16/695,622 mailed Mar. 7, 2022 (19 pages).

"Response to Communication Pursuant to Rules 161(1) and 162 EPC," for European Patent Application No. 19839060.1 filed Aug. 10, 2021 (10 pages).

"Final Office Action," for U.S. Appl. No. 16/717,113 mailed Oct. 19, 2022 (24 pages).

"Response to Final Office Action," for U.S. Appl. No. 16/717,113, filed on Dec. 8, 2022 (11 pages).

"Response to Non-Final Office Action," for U.S. Appl. No. 16/717,113, filed on Jul. 21, 2022 (11 pages).

"Non-Final Office Action," for U.S. Appl. No. 16/717,113 mailed Feb. 2, 2023 (36 pages).

"Response to Non-Final Office Action," for U.S. Appl. No. 16/717,113, filed on Apr. 28, 2023 (15 pages).

Choi, C., et al."Wettability Effects on Heat Transfer," IntechOpen 2011 (33 pages).

"Final Office Action," for U.S. Appl. No. 16/717,113 mailed Aug. 16, 2023 (36 pages).

"Notice of Allowance," for U.S. Appl. No. 16/717,113 mailed Nov. 13, 2023 (12 pages).

"Response to Final Office Action," for U.S. Appl. No. 16/717,113, filed on Oct. 3, 2023 (13 pages).

"First Office Action," for Chinese Patent Application No. 201980084406.3 (our file 115.0345CNWO) mailed Apr. 11, 2024 (6 pages) no English translation.

* cited by examiner

CLOSED IRRIGATED RADIOFREQUENCY BIPOLAR TINED ABLATION PROBE

This application is a continuation of U.S. patent application Ser. No. 16/695,622, now U.S. Pat. No. 11,382,682 filed Nov. 26, 2019, this application claims the benefit of U.S. Provisional Application No. 62/772,421 filed Nov. 28, 2018, the content of which is herein incorporated by reference in its entirety.

BACKGROUND

Radiofrequency ablation is used in the treatment of medical conditions, including the treatment of tumors. In this context, one goal of radiofrequency ablation is to destroy the tumor, forming a lesion. Radiofrequency ablation heats and dehydrates tissue, causing necrosis and tissue charring. Cooling the tissue or the ablation electrodes is sometimes desirable.

SUMMARY

Some examples of the disclosed technology provide a closed loop irrigated ablation system. The system includes an ablation probe defining a central channel with a distal opening. The ablation probe has an outer sheath with a lumen. The outer sheath includes an outer electrode that at least partially defines an outer surface of the probe and that at least partially defines the lumen of the outer sheath. The outer electrode is defined on the outer surface between insulated portions of the outer sheath. The probe further includes a tubing disposed in the lumen and coaxial with the outer sheath. An electrode array assembly is disposed inside an inner diameter of the tubing. The electrode array assembly has a retracted configuration in which an electrode array is within the central channel of the ablation probe and a protruded configuration in which the electrode array protrudes from the distal opening of the central channel. The probe further includes a closed irrigation path. The irrigation path has a first segment at least partially defined by the tubing and a second segment at least partially defined between an outer surface of the tubing and an inner surface of the outer electrode. The system further includes a coolant source configured to deliver a cooling fluid to the closed irrigation path and receive circulated cooling fluid from the closed irrigation path.

In some examples, the outer sheath comprises a conductive shaft partially covered by an insulator, and the outer electrode is an exposed axial section of the conductive shaft. In some examples, the outer electrode is a ring electrode and the ablation probe comprises electrical leads connected to the ring electrode. In some examples, the outer electrode comprises a textured inner surface. In some examples, the inner surface of the outer electrode is coated with a wetting agent. In some examples, the system is configured so that the first segment forms a portion of an inlet path for the cooling fluid moving toward a distal end of the ablation probe, and the irrigation path is configured so that the second segment forms a portion of an outlet path for the cooling fluid moving toward a proximal end of the ablation probe. In some examples, the first segment and second segment of the irrigation path are concentric. In some examples, the tubing comprises an inner surface defining a tubing lumen and the first segment is defined by the inner surface of the tubing. In some examples, the first segment is at least partially defined within a wall of the tubing. In some examples, the wall of the tubing comprises at least four passages defining portions of the first segment. In some examples, the tubing has a corrugated outer surface comprising corrugations. In some examples, the tubing outer surface directs the coolant to flow in a non-linear path, such as helically around the outer surface of the tubing. In some examples, the tubing has a non-uniform thickness. In some examples, the tubing is a polymer tube or an insulated stainless steel tube. In some examples, the ablation probe further comprises a liner concentric with and within the tubing, wherein the first segment of the irrigation path is defined between the inner surface of the tubing and an outer surface of the liner. In some examples, the liner defines the central channel of the ablation probe. In some examples, the electrode array assembly has three or more electrode tines at a distal end of the electrode array assembly.

In other aspects of the disclosed technology, a closed loop irrigated ablation system includes an ablation probe defining a central channel with a distal opening. The ablation probe has an outer sheath with a lumen. The outer sheath has a conductive shaft partially covered by an insulator. An exposed portion of the conductive shaft forms an outer electrode, and the inner surface of the conductive shaft defines the lumen. The probe further includes a tubing disposed in the lumen and coaxial with the outer sheath and a liner concentric with and within the tubing. An inner surface of the liner defines the central channel of the ablation probe. The probe further includes an electrode array assembly disposed inside the inner surface of the liner, the electrode array assembly having a retracted configuration where an electrode array is within the central channel of the ablation probe and a protruded configuration where the electrode array protrudes from the distal opening of the central channel. A closed irrigation path within the probe has a first segment at least partially defined by the inner surface of the tubing and the outer surface of the liner, and a second segment at least partially defined between an outer surface of the tubing and an inner surface of the outer electrode. The system further includes a coolant source configured to deliver a cooling fluid to the closed irrigation path and receive circulated cooling fluid from the closed irrigation path.

In other aspects of the technology, a radiofrequency ablation method is provided. The method includes providing an ablation probe defining a central channel with a distal opening, the ablation probe comprising an outer sheath having a lumen, an outer electrode at least partially defining an outer surface of the probe and at least partially defining the lumen, wherein the outer electrode is defined on the outer surface between insulated portions of the outer sheath. The probe further includes a tubing disposed in the lumen and coaxial with the outer sheath. The probe further includes an electrode array assembly disposed inside an inner diameter of the tubing. A closed irrigation path within the probe has a first segment at least partially defined by the tubing and a second segment at least partially defined between an outer surface of the tubing and an inner surface of the outer electrode. The method further includes moving the electrode array assembly between a retracted configuration where an electrode array is within the central channel of the ablation probe and a protruded configuration where the electrode array protrudes from the distal opening of the central channel. The method includes attaching a coolant source to the closed irrigation path, providing fluid flow through the closed irrigation path, and attaching the electrode array and outer electrode to a generator and providing radiofrequency current flow between the electrode array and the outer electrode.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense.

Figure 1:
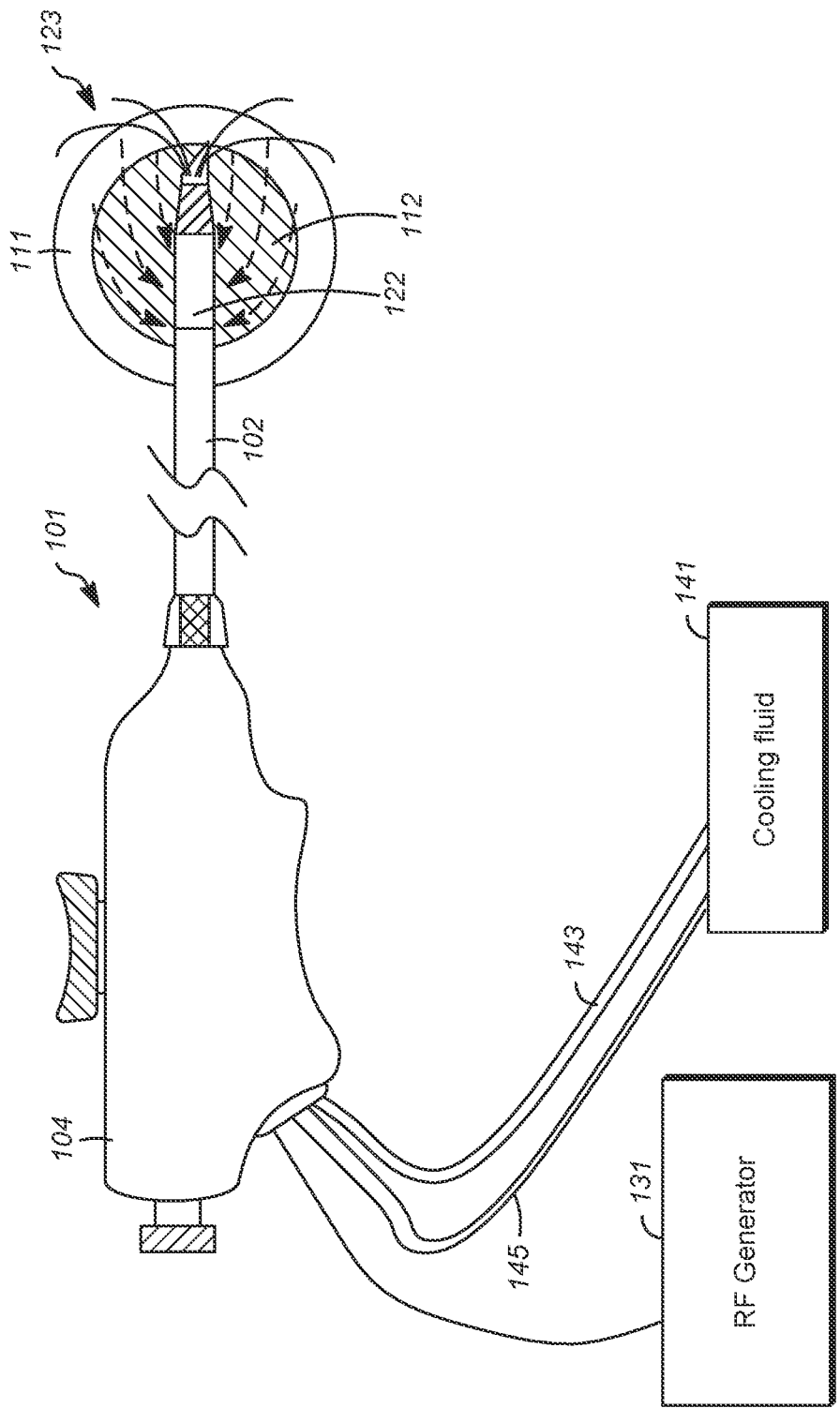
FIG. 1 is a schematic view of a closed loop irrigated ablation system according to some examples.

While embodiments herein are susceptible to various modifications and alternative forms, specifics thereof have been shown by way of example and drawings, and will be described in detail. It should be understood, however, that the scope herein is not limited to the particular examples described. On the contrary, the intention is to cover modifications, equivalents, and alternatives falling within the spirit and scope herein.

DETAILED DESCRIPTION

This disclosure describes a closed irrigated bipolar radiofrequency ablation probe. The bipolar electrodes can include a shaft electrode and an expandable array of electrode tines. A closed loop irrigation channel is provided inside of the shaft body of the probe to cool the shaft electrode. Closed irrigation can be used in situations where saline distribution within tissue is not desirable, such as inside the lung. In lung tumor ablation, breath movement in the lungs makes it desirable to have a tined electrode to hold the position of the ablation probe without damage to other organs. The described radiofrequency ablation system enhances lesion formation for soft tissue ablation. The system can improve ablation performance over existing radiofrequency ablation systems.

Various examples of the technology provide an ablation system that includes an ablation probe with a closed cooling system. A cooling fluid inside the ablation probe takes heat away from the electrode. This slows the heating next to the surrounding tissue to reduce or prevent tissue charring during radiofrequency ablation. Some examples of the ablation probe have a closed irrigation path with a first segment and a second segment. In some examples, the first segment of the irrigation path is an inflow segment and is closer to the linear axis of the ablation probe than a second, outflow segment of the irrigation path. This allows a cooling fluid to flow into the probe through a central portion of the probe body and exit the probe through an outer portion of the probe body. Fluid that has been warmed up through contacting the electrodes is able to flow back out of the probe using the shortest route rather than traveling to the distal end before starting its trip out of the probe.

Radiofrequency current is applied between the shaft electrode and the expandable electrode array. The shaft electrode is sealed on the shaft so cooling fluid can flow near the inner surface of the electrode to cool the electrode but cooling fluid cannot flow into the patient tissue. In some examples, the irrigation path includes an inlet path and an outlet path that are coaxial. In some example, the cooling fluid inlet path is nearer to the center axis of the probe, and the outlet path is nearer to the outer surface of the probe and adjacent to the electrode's inner surface. This can allow efficient cooling, because the cooling fluid entering the probe is separated from the warmth of the patient tissue surrounding the ablation probe by the fluid in the outlet path.

As used herein, the words proximal and distal express a relationship between two different elements. An element that is designated as being proximal is positioned closer to the external portion of the system, i.e., a portion that does not enter a patient's body. An element that is designated as being distal is positioned closer to the insertion end of the system. As used herein, axial motion refers to movement of an object in a direction along the axis of the device.

Closed Loop Irrigated Ablation System

Turning to the drawings, FIG. 1 is a schematic view of a closed loop irrigated ablation system according to some examples. The system 101 includes an ablation probe 102 operatively connected to a handle 104 for manual manipulation of the ablation probe 102. In some examples, the ablation probe 102 has an outer electrode 122 and an electrode array 123 configured for bipolar radiofrequency ablation. A radiofrequency energy source 131 is configured to deliver radiofrequency energy to the electrodes to ablate patient tissue to form a lesion 111. The radiofrequency energy source 131 can be, for example an RF3000™ Generator, manufactured by Boston Scientific, Inc. of Marlborough, Mass. A cooling fluid reservoir 141 is connected to the ablation system to deliver cooling fluid into the system through a first conduit 143 and to receive circulated fluid out of the system through a second conduit 145. In some examples, the cooling fluid is a saline solution. In alternative examples, the cooling fluid can be deionized water. It is also possible to use other cooling fluids, and these equivalents fall within the scope of the disclosed technology.

FIG. 1 schematically shows the ablation system 101 positioned to deliver ablation energy to ablate patient tissue to form a lesion 111 near and surrounding a tumor 112. A distal end of the ablation probe 102 is placed within or near the tumor 112. The lesion 111 represents tissue to be ablated. Tines 123 are deployed into the patient tissue 112 and radiofrequency energy is supplied between the tines 123 and outer electrode 122. The outer electrode 122 is positioned on an outer surface of a shaft of the ablation probe and can also be referred to as a shaft electrode.

An irrigation source 141 is used to inject a cooling fluid through the probe 102 to circulate in a closed loop inside of the probe 102 to cool the electrode 122 without delivering cooling fluid into the patient tissue. When radiofrequency energy is transferred into patient tissue, the shaft electrode 122 is heated. The cooling fluid circulating inside of the probe 102 regulates the temperature of the electrode 122, reducing overheating in the tissue directly adjacent to the electrode 122. This can slow excessive heating and prevent or reduce tissue charring near the electrode 122.

Figure 2:
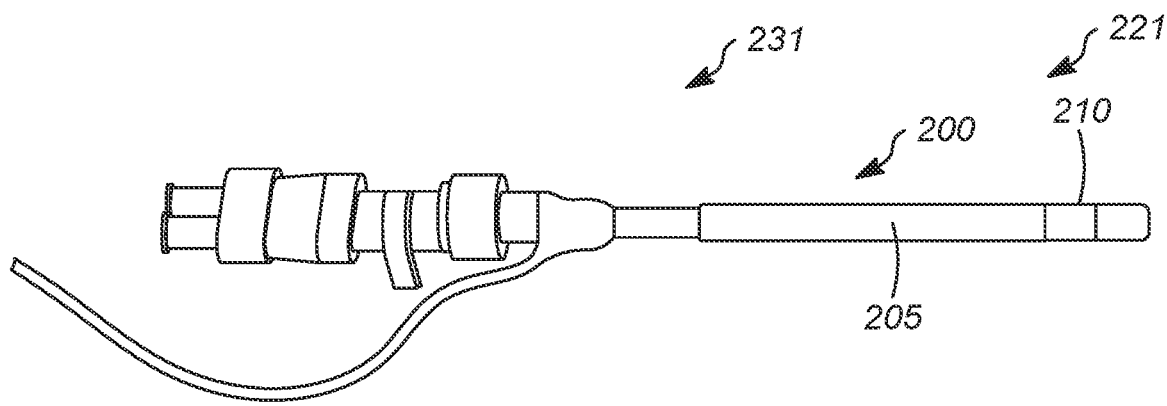
FIG. 2 is a side view of outer sheath for a closed loop irrigated ablation system according to some examples.

FIG. 2 is a side view of an outer sheath for a closed loop irrigated ablation system according to some examples. The outer sheath 200 has a distal end 221 and a proximal end 231. The outer sheath 200 can be used as part of the system shown in FIG. 1. In FIG. 2, the tines 123 of the electrode array assembly are not protruding from the distal end 211 of the outer sheath 200. The outer sheath 200 includes an electrode 210 that partially defines the outer surface 205 of the outer sheath 200. In some examples, the outer sheath 200 includes a central lumen comprising a central channel (not seen in FIG. 2), that is configured to receive an electrode assembly that can be introduced into and is slidably movable within the central lumen of the outer sheath 200 during a treatment procedure. In some examples, the central channel of the outer sheath 200 can be used in combination with a stylet having a tissue-piercing tip to facilitate insertion of the outer sheath 200 into patient tissue.

Figure 3:
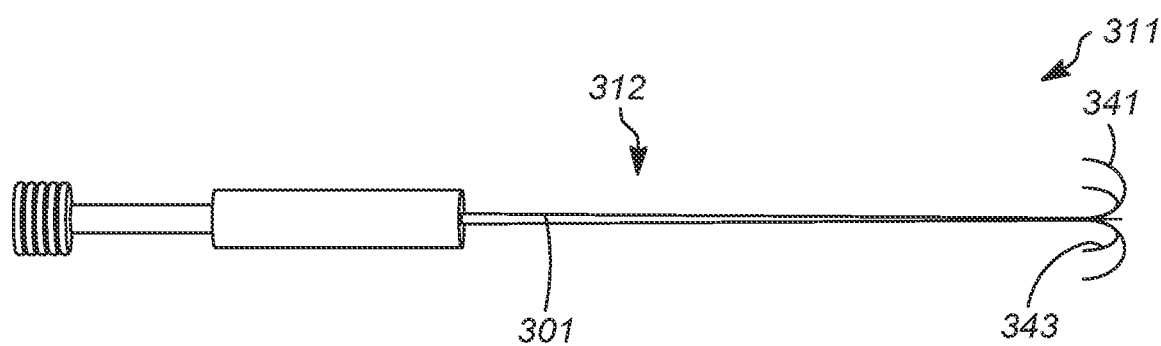
FIG. 3 is a side view of an electrode assembly for use with the outer sheath of FIG. 2 in a closed loop irrigated ablation system according to some examples.

FIG. 3 shows one example of an electrode assembly 301 for use with the outer sheath 200. The outer sheath 200 in combination with the electrode assembly 301 provide a functional bipolar ablation device. The electrode array assembly 301 has a distal end 311 and a proximal end 312. At the distal end 311 of the electrode assembly 301 is an electrode array 343 configured for tissue ablation. The electrode array assembly 301 is shown in FIG. 3 in its protruded configuration where the electrode array 343 protrudes from the shaft 314 at the distal end 311 of the electrode assembly. The electrode array assembly 301 also has a retracted configuration (not seen in FIG. 3) in which the electrode array 343 is within a shaft 314 of the electrode assembly 301, which would appear similar to FIG. 3 but without the electrode array 343 protruding from the distal end 311.

One example of an electrode array assembly that can be used with the systems described herein is the LEVEEN COACCESS™ Needle Electrode, commercially available from Boston Scientific Corporation, Inc. of Marlborough, Mass.

In some examples, the electrode array 343 is made of a shape memory material, such as Nitinol. The electrode array 343 can be made up of a plurality of individual tines 341. In some examples, the electrode array 343 includes at least three tines 341. When the electrode array 343 is retracted inside of the shaft 314 of the electrode assembly 301, the individual tines 341 of the electrode array 343 straighten to fit the interior of the lumen. When the electrode array 343 is deployed outside of the shaft 314 of the electrode assembly 301, the tines 341 resume a preset shape. In the example of the FIGS., the preset shape is arcuate. In alternative examples, the electrode array assembly 301 can have a straight or angled shape.

When the electrode assembly 301 of FIG. 3 is positioned within the ablation probe 200 of FIG. 2, then the distal end 311 of the electrode assembly 301 is positioned near the distal end 221 of the ablation probe 200. As a result, when the electrode array 343 is moved into its protruded configuration then it protrudes not only from the shaft 314 of the electrode assembly 301, but also from the distal end 221 of the ablation probe 200, as shown in FIG. 1.

Figure 4:
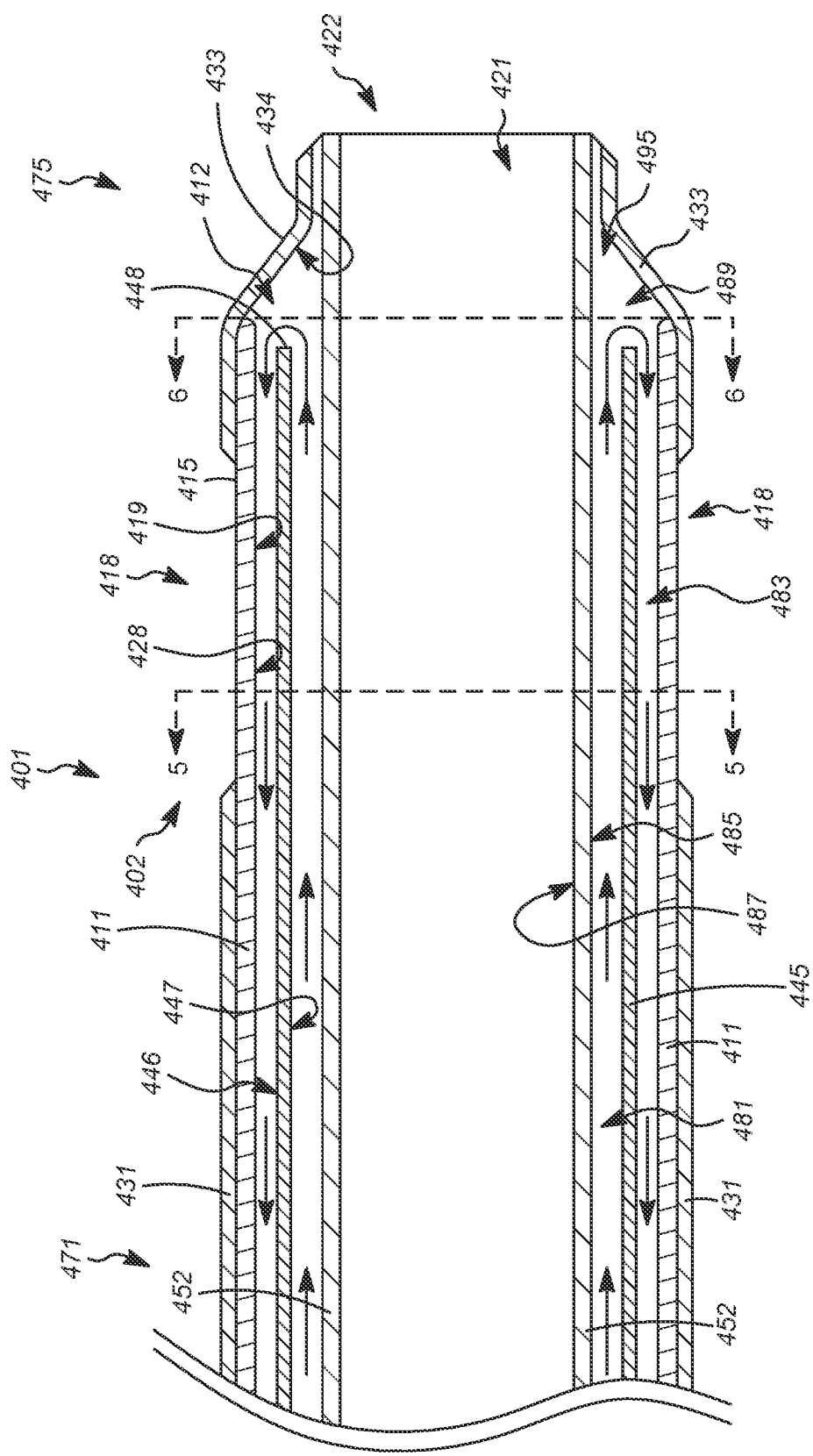
FIG. 4 is a cross-sectional view of an outer sheath of a closed loop irrigated ablation probe according to some examples.

FIG. 4 is a cross-sectional view of a closed loop irrigated ablation probe according to some examples. The ablation probe 401 has an outer sheath 411 defining a lumen 412. The outer sheath 411 has an outer surface 415 that can define an electrode 418 that is electrically conductive. In some examples, a proximal insulator 431 is provided on the outer surface 415 of the outer sheath 411 at the proximal end 471 of the probe 401. In some examples, a distal insulator 433 is provided at the distal end 475 of the probe 401.

In some examples, the outer sheath includes a conductive shaft made of an electrically conductive material such as stainless steel. In the example of FIG. 4, the electrode 418 is an exposed section of the outer sheath 411. The electrode 418 can be at least partially defined by the outer surface 415 of the outer sheath 411 between the proximal insulator 431 and the distal insulator 433. Thus, an outer surface 402 of the probe 401 is defined at least partially by the electrode 418.

In one example, the outer sheath 411 has an outer diameter of at least about 0.01 inch (0.25 mm), at least about 0.03 inch (0.76 mm), at most about 0.3 inch (7.62 mm), at most about 0.1 inch (2.54 mm), and about 0.039 inch (0.99 mm). In one example, the outer sheath 411 has an inner diameter of at least about 0.01 inch (0.25 mm), at least about 0.03 inch (0.76 mm), at most about 0.3 inch (7.62 mm), at most about 0.1 inch (2.54 mm), and about 0.033 inch (0.84 mm). In one example, the outer sheath has a wall thickness of about 0.006 inch (0.15 mm). It will be appreciated that many other dimensions are possible for the outer sheath.

In the example of FIG. 4, the electrode 418 also partially defines the lumen 412 of the outer sheath 411. In other words, the inner surface 428 of outer sheath 411 is continuous with the inner surface 419 of the electrode 418, which is open to the lumen 412. As will be discussed below, this allows a cooling fluid to draw heat away from the electrode 418. In some examples, the inner surface 419 of the electrode 418 is coated with a wetting agent to increase the amount of heat conducted away by the cooling fluid.

The example of FIG. 4 shows the insulators 431, 433 as having an outer diameter that is thicker than the outer diameter of the electrode 418 and having a chamfer cut edge angled toward the electrode surface. In alternative examples the probe can be manufactured to make the outer surface 415 of the outer sheath 411 flush with the outer surface of the insulators 431, 433, giving the outer surface 402 of the probe 401 a uniform outer diameter. In one example, the electrode 418 portion of the outer sheath 411 is thicker than the insulated portions of the outer sheath so that the outer surface of the electrode is flush with the outer surface of the remainder of the outer sheath.

The ablation probe 401 further includes a liner 452 disposed inside of the lumen 412 of the outer sheath 411. The liner 452 defines a central channel 421 that has a distal opening 422. In some embodiments, the central channel 421 is configured to slidably receive the electrode array assembly 301 described in relation to FIG. 3. In this embodiment, the electrode array assembly 301 can be inserted into a proximal end of the central channel 421. Once inserted, the distal end of the electrode array assembly 301 will line up with or be very close to the distal end of the ablation probe. The liner 452 has an outer surface 485 and an inner surface 487.

In some examples, the liner 452 can be made of an insulating material such as a polymer tube. Other example materials include fluoropolymers. The liner 452 can have an outer diameter of between about 0.020 inches (0.508 mm) and 0.100 inches (2.540 mm), with the understanding that the outer diameter of the liner 452 is smaller than the inner diameter of the outer sheath 411. The liner 452 can have an inner diameter of between about 0.019 inches (0.483 mm)

and 0.099 inches (2.513 mm). The liner 452 can have a wall thickness of between about 0.00025 inch (0.00635 mm) and 0.015 inch (0.381 mm).

In the example of FIG. 4, a tubing 445 is disposed between the outer sheath 411 and the liner 452 to define the irrigation path. The tubing 445 is coaxial with the outer sheath 411, and coaxial with the liner 452. The tubing 445 is situated within the ablation probe 401 such that it can surround the electrode array assembly 301 when the electrode array assembly 301 is inside of the central channel 421. The tubing 445 has an outer surface 446 and an inner surface 447. The inner surface 447 of the tubing 445 defines a tubing lumen. The tubing 445 separates the irrigation path into two segments.

In some examples, the tubing 445 has a wall thickness of 0.001 inches (0.025 mm) or less. In some examples, the tubing 445 has a wall thickness of between about 0.001 inches (0.025 mm) and 0.004 inches (0.102 mm).

The tubing 445 can be made of an electrically insulating material such as a polymer with a sufficiently high melt temperature to withstand heat from the electrode 418. Some example materials include fluoropolymers or polyamide. A polyamide tubing 445 can have a wall thickness of about 0.001 inch (0.025 mm), less than 0.001 inch (0.025 mm), at least about 0.001 inch (0.025 mm), or at least about 0.001 (0.025 mm) inch and at most about 0.002 inch (0.051 mm). A polymer tubing 445 can have a wall thickness of about 0.003 inch (0.076 mm), at least about 0.003 inch (0.076 mm), or at least about 0.003 inch (0.076 mm) and at most about 0.004 inch (0.102 mm). In alternative examples, the tubing 445 can be constructed from an insulated conductive material such as stainless steel tubing or Nitinol tubing with an insulating coating. A stainless steel or Nitinol tubing can have a wall thickness of at least about 0.002 inch (0.051 mm), between about 0.002 inches (0.051 mm) and about 0.004 inches (0.102 mm), between about 0.003 inches (0.076 mm) and about 0.004 inches (0.102 mm), or at most about 0.004 inch (0.102 mm).

In some examples, the inner diameter of the tubing 445 is at least 0.001 inches (0.025 mm) greater than the outer diameter of the liner 452. In some examples, the inner diameter of the tubing 445 is less than about 0.005 inches (0.127 mm) greater than the outer diameter of the liner 452. In some examples, the inner diameter of the outer sheath 411 is at least 0.001 inches (0.025 mm) greater than the outer diameter of the tubing 445, and less than 0.005 inches (0.127 mm) greater than the outer diameter of the tubing 445.

In the example of FIG. 4, the ablation probe 401 defines a closed irrigation path between the inner surface 428 of the outer sheath 411 and the outer surface 485 of the liner 452. More particularly, the closed irrigation path 489 has a first segment 481 that is partially defined between the tubing 445 and the liner 452, and a second segment 483 that is partially defined between the outer surface 446 of the tubing 445 and the inner surface 419 of the electrode 418. In some embodiments, the first segment 481 is a portion of the inlet path and the second segment 483 is a portion of the outlet path, as indicated by the arrows in FIG. 4. In other embodiments, the opposite is true so that the first segment 481 is a portion of the outlet path and the second segment 483 is a portion of the inlet path.

In the example of FIG. 4, the first segment inlet path and the second segment outlet path are concentric. In alternative examples, the inlet path and the outlet path do not have to be concentric.

In some examples, there is a fluid-tight seal between the distal insulator 433 and the rest of the outer sheath 411, and between the distal insulator 433 and the liner 452 at the distal end 475 of the probe 401. The closed irrigation path 489 is further defined in a turn space 495 between the outer surface 485 of the liner 452 and the inner surface 434 of the distal insulator 433, where the irrigation path 489 leaves the first segment 481 and turns the corner to go out the second segment 483.

Figure 5:
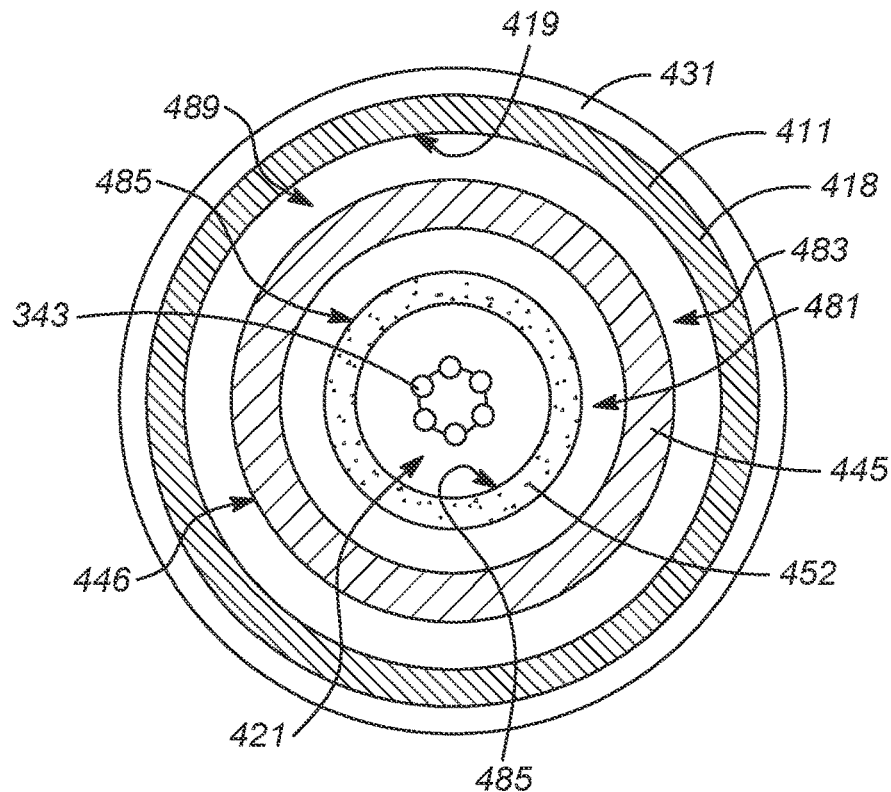
FIG. 5 is a cross-sectional view of the outer sheath of FIG. 4 along line 5-5 of FIG. 4 according to some examples.
Figure 6:
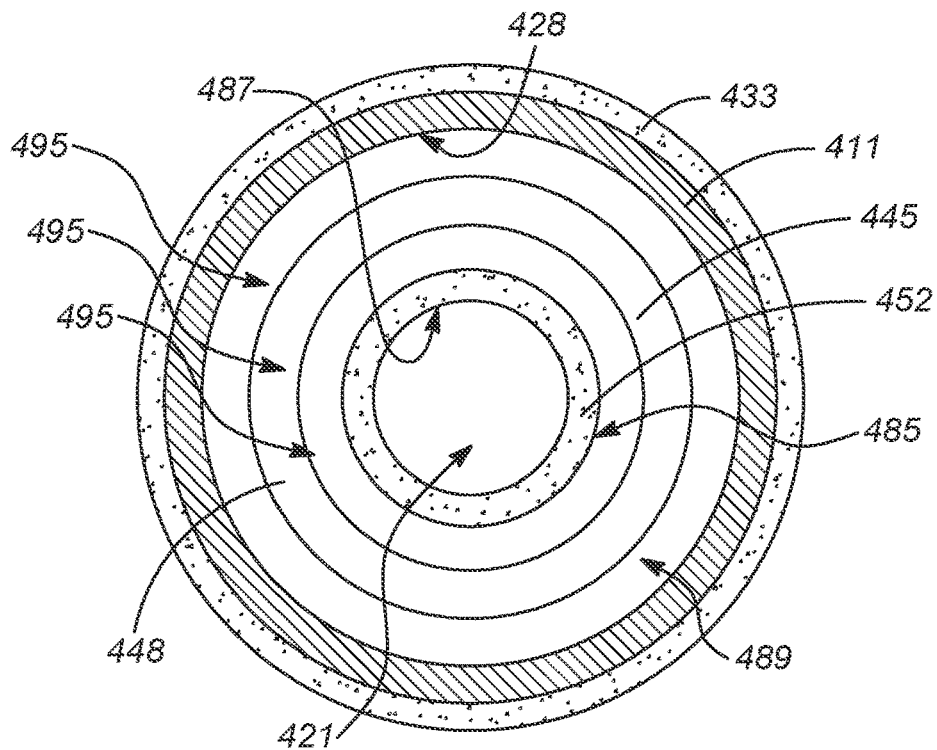
FIG. 6 is a cross-sectional view of the outer sheath of FIG. 4 along line 6-6 of FIG. 4 according to some examples, with the electrode assembly of FIG. 3.

For ease of illustration, FIGS. 4 and 6 do not show an electrode assembly present in the central channel of the probe. However, during use, an electrode array assembly with an expandable electrode array would be present inside the central channel of the probe. FIG. 5 does show the electrode array 343 inside the central channel 421 of the probe. In the example of FIG. 5, the electrode array 343 is retracted inside of the central channel. During an ablation procedure, the electrode array would be extended outside of the central channel 421, similar to the example of FIG. 1.

FIGS. 5 and 6 are cross-sectional views of the ablation probe 401 that further illustrate the components of and fluid flow path of the ablation probe 401, including the turn space 495. FIG. 5 is a cross-sectional view of the ablation probe 401 along line 5-5 of FIG. 4 through the portion of the ablation probe 401 containing the electrode 418 and the tubing 445. FIG. 6 is a cross-sectional view of the ablation probe 401 along line 6-6 of FIG. 4, through the turn space 495 that comprises a void for fluid flow between the liner 452 and the distal insulator 433. The cross-sectional view of FIG. 6 is distal to the distal end of the tubing 445, so an end view of tubing 445 is seen rather than a cross-section.

Referring now to FIGS. 1 and 4-6, a circuit of cooling fluid flows from the cooling fluid reservoir 141, into the first conduit 143, and then into the first segment 481 of the closed irrigation path 489, so that the first segment 481 forms a portion of an inlet path for the cooling fluid. The inlet path starts near the proximal end 471 of the ablation probe 401, and extends toward the distal end 475 of the ablation probe 401. At the distal end 475 of the ablation probe 401, the irrigation path 489 turns in the turn space 495 between the distal insulator 433 and the liner 452. Cooling fluid is then forced into the second segment 483, which is an outlet path that conveys the cooling fluid out of the proximal end 471 of the ablation probe 401, through the second conduit 145, and back to the cooling fluid reservoir 141.

In some examples, a positive pressure forces fluid through the first conduit 143 into the body of the probe. In some examples, a negative pressure pulls fluid from out of the probe body and through the second conduit 145 and back to the cooling fluid reservoir 141. In some examples, both positive pressure in the first conduit 143 and negative pressure in the second conduit 145 are provided. In some examples, the cooling reservoir is configured to re-cool the cooling fluid received through the second conduit 145 and recirculate the cooling fluid into the system again. In some examples, the cooling fluid is not recirculated.

In the example of FIG. 4, the distal tip 448 of the tubing 445 ends before the distal tip of the probe, creating a void in the turn space 495. In alternative examples of the technology (not shown), the distal tip of the tubing can extend all the way to the inner surface 434 of the distal insulator 433, such that the tubing 445 partially obstructs the closed irrigation path. In some examples, a separate structure such as a connecting member is provided (not shown), and the connecting member can bridge the space between the tubing 445 and the inner surface 434. In either case, the closed irrigation path 489 is obstructed by these physical structures, but passages are provided through the structure. The passages connect the inlet path and the outlet path. In this case, the fluid pressure difference between the inlet path and the outlet path forces cooling fluid through the passages, allowing fluid to flow through the cooling flow circuit.

Alternative Example of a Closed Irrigated Ablation Probe

Figure 7:
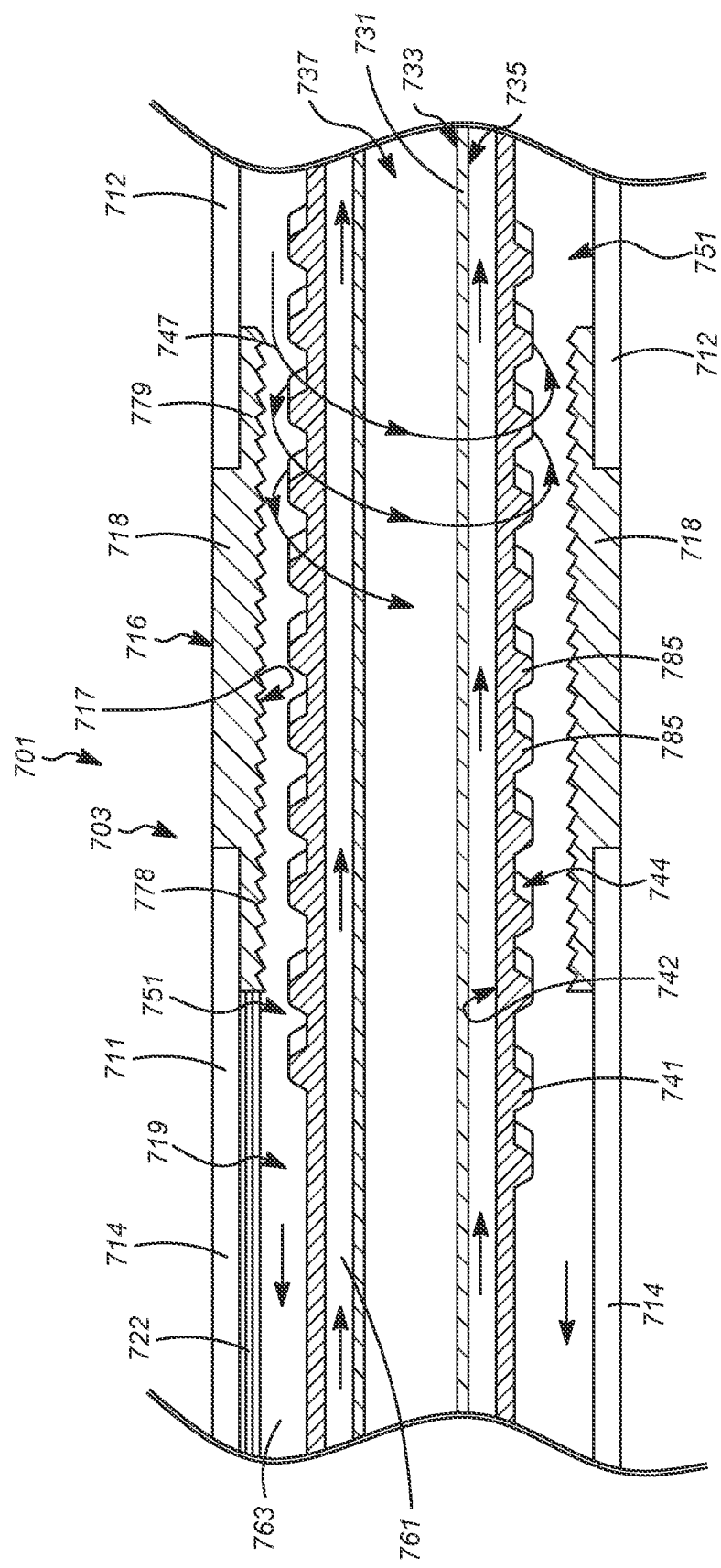
FIG. 7 is a cross-sectional view of an alternative example of an outer sheath of a closed loop irrigated ablation probe according to some examples.

In alternative examples of the disclosed technology, the geometry of the tubing causes the cooling fluid to follow a nonlinear path through the body of the ablation probe. In alternative examples of the disclosed technology, the outer electrode is a segment of conductive material. FIG. 7 is a cross-sectional cutaway view of an alternative example of a closed loop irrigated ablation probe according to these and other alternative examples. FIG. 7 shows a middle section of the ablation probe 701. In practice, the probe 701 can include a distal end (not shown in FIG. 7) similar to the distal end 475 of the probe 401 and its alternatives, and the probe 701 can be connected to a handle in an ablation system such as that shown in FIG. 1.

The ablation probe 701 includes an outer sheath 711 that itself includes an outer electrode 718. In some examples, the outer electrode 718 is a cylindrical ring electrode connected between a distal insulating portion 712 that is distal to the electrode 718, and a proximal insulating portion 714 that is proximal to the electrode 718. The electrode 718 is a substantially cylindrical tube, surrounded by insulating material on both ends of the tube. In the example of FIG. 7, the electrode 718 is a different structure from the outer sheath 711. The electrode 718 is attached to the inner surface of the proximal insulating portion 714 at a first wing portion 778 of the electrode 718, and to the insulating distal portion 712 at a second wing portion 779 of the electrode 718. The wing portions 778, 779 extend under and overlap with the adjacent insulating material. The wing portions 778, 779 are thinner than a central part of the electrode. One or more conductive leads 722 electrically connect the electrode 718 to a radiofrequency energy generator. The outer sheath 711 defines a lumen 719 through which a cooling fluid can flow.

An outer surface 716 of the electrode 718 at least partially defines the outer surface 703 of the ablation probe 701. An inner surface 717 of the electrode 718 at least partially defines a lumen 719. As can be seen from FIG. 7, the electrode 718 is defined on the outer surface 703 between the insulating distal portion 712 and the insulating proximal portion 714 of the outer sheath 711.

In some examples, the outer electrode 718 is a simple cylinder of conducting material of uniform thickness joined to the insulating segments 712, 714 with a butt-weld. In the example of FIG. 7, the electrode 718 includes overlapping segments 779, 778 that extend distally and proximally of the main electrode portion and overlap with the distal insulating portion 712 and the proximal insulating portion 714, respectively. The overlapping segments of the electrode can be welded or otherwise attached to the inner surfaces of the insulating portions.

In some examples, the inner surface 717 of the electrode 718 has a non-smooth surface. The surface texture of the inner surface 717 creates a larger surface area for contact between the inner surface 717 of the electrode and a cooling fluid flowing through the lumen 719. In addition or alternatively, the inner surface 717 of the outer electrode 715 may benefit from being coated with a wetting agent to further improve contact between the electrode 718 and the cooling fluid. This optional feature, described in more detail herein, allows the cooling fluid to more effectively draw heat away from the electrode 718.

In some examples, the ablation probe 701 further includes a liner 731 having an inner surface 733 and an outer surface 735. The inner surface 733 of the liner 731 can define a lumen 737 through which an electrode array can be deployed. The lumen 737 can define a central channel through which the electrode assembly is slidably movable along an axis of the ablation probe 701.

The ablation probe 701 also includes a tubing 741 disposed in the lumen 719 that is coaxial with the outer sheath 711. The tubing 741 has an inner surface 742 and an outer surface 744. In some examples, the tubing 741 is constructed from an insulating material. In alternative examples, the tubing 741 is constructed from a metal such as stainless steel, which may have an electrically insulating coating. The tubing 741 is configured such that an electrode array assembly can be disposed inside of the inner diameter of the tubing 741. In the example of FIG. 7, the liner 731 is concentric with the tubing 741 inside of the inner diameter of the tubing 741, and an electrode array assembly can be disposed inside of both the liner 731 and the tubing 741.

In addition or alternatively, the tubing 741 has a plurality of corrugations 785 on the outer surface 744 of the tubing 741. The corrugations 785 give the tubing 741 a non-uniform thickness. In the example of FIG. 7, the corrugations 785 wrap around the exterior of the tubing 741 helically according to arrows 747, similar to a threaded screw. The corrugated outer surface 744 of the tubing 741 directs cooling fluid to flow helically around the outer surface 744 of the tubing 741. The directed flow path, such as a helically directed flow path, reduces the likelihood of dead spots in the irrigation path. As a result, there is a reduced likelihood of uneven cooling. In some examples, the corrugations 785 comprise alternating peaks and troughs. In some examples, the tubing 741 has a minimum wall thickness of about 0.001 inches (0.025 mm). In some examples, the peaks of the corrugations 785 increase the wall thickness of the tubing 741 by about 0.001 inches (0.025 mm). In some examples, the distance between adjacent corrugations 785 is between about 0.0005 inches (0.0127 mm) and 0.020 inches (0.508 mm). In some examples, the tubing 741 has between about 1000 corrugations per inch (394 corrugations per cm) and 4 corrugations per inch (1.6 corrugations per cm). In some examples, the peaks of the corrugations 785 have a flattened shape. In alternative configurations, the peaks of the corrugations 785 can have other shapes, such as rounded, triangular, etc.

The ablation probe 701 is provided with a closed irrigation path. The irrigation path 751 has a first segment 761 and a second segment 763. In some examples, the first segment 761 is an inlet path that receives cooling fluid from an external cooling fluid reservoir. In some examples, the second segment 763 is an outlet path that directs fluid to flow out of the ablation probe 701. In FIG. 7, the outer sheath 711, the tubing 741, and the liner 731 are concentric around an axis of the probe 701. Corrugations 785 in the tubing 741 are configured to direct fluid flow helically around the axis as illustrated by the arrows 747. The example of FIG. 7, where the direction of fluid flow is diagonal to the axis of the probe 701, allows the same amount of fluid to spend a longer amount of time in contact with the inner surface 717 of the electrode 718 compared to the example of FIG. 4, where fluid is directed in a path parallel to the axis of the probe 701. In the drawing of FIG. 7, the corrugations 785 are present on only a portion of the tubing 741. In alternative examples, a different portion of the tubing 741 or the entire outer surface 744 of the tubing 741 can contain corrugations. In some examples, the corrugations 785 create a fluid dynamic in which there is a high pressure drop across the irrigation path between the first segment and the second segment. This causes an increased flow velocity of the fluid along the helical path effected by the corrugations 785.

Tubing Having a Plurality of Wall Passages

Figure 8:
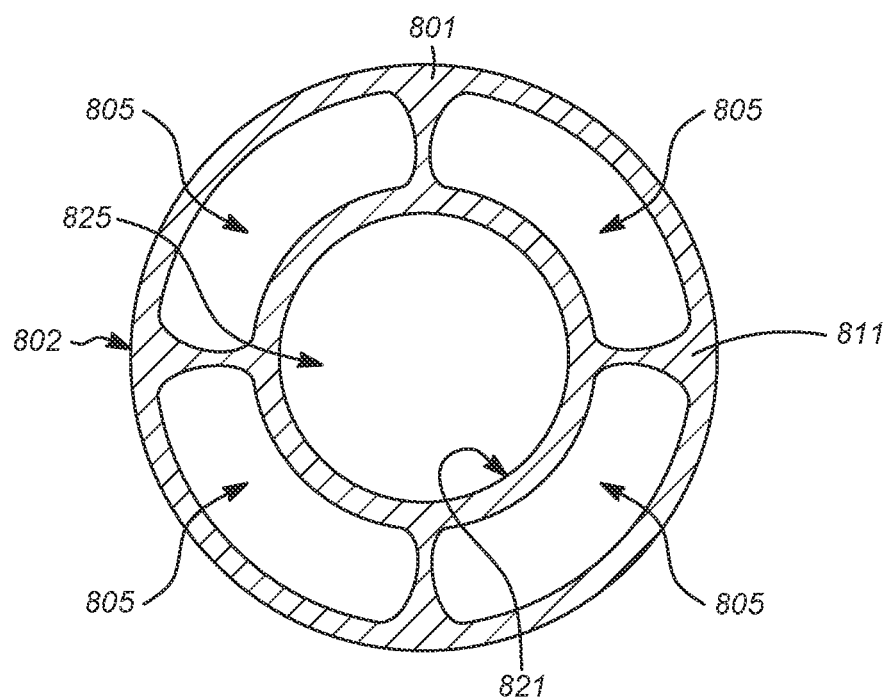
FIG. 8 is a cross-sectional view of a tubing for a closed loop irrigation ablation probe according to some examples.

Other configurations are contemplated for the tubing to be used with the closed loop irrigated ablation system. FIG. 8 is a cross-sectional view of a tubing that has a plurality of passages extending axially along the length of the tubing in a wall of the tubing. In particular, FIG. 8 shows a tubing 801 having a plurality of passages 805. The passages 805 are defined within a wall 811 of the tubing 801. In the example of FIG. 8, the tubing 801 contains four passages 805. The tubing wall 811 defines openings (not shown) near the tubing 801 distal end to allow the fluid communication with the passages 805. In some examples, at least one of the passages is an inlet path forming a first segment of a closed loop irrigation path.

In one example, each of the passages 805 provide inlet paths of the irrigation path and the outlet path is defined between an outer surface 802 of the tubing 801 and an inner surface of an outer sheath including an outer shaft electrode (not shown) surrounding the outside of the tubing 801. In one example, at least one of the passages is an outlet path forming a second segment of a closed loop irrigation path. In some examples, two of the passages 805 form the first segment inlet path, and two of the passages 805 form the second segment outlet path.

In some examples, the wall 811 of the tubing 801 is about 0.007 inches (0.178 mm) thick, and the passages span about 0.005 inches (0.127 mm) of the thickness of the wall 811, creating a thickness of about 0.001 inches (0.025 mm) between the passage and the outer surface 802 of the tubing 801.

In some examples, the tubing 801 has an interior surface 821 defining an inner lumen 825. The inner lumen 825 can be used in addition to, or in place of, a liner such as the liner 452 of FIG. 4 or the liner 731 of FIG. 7. The liner 452 or the liner 731 can be eliminated from the probe if the inner lumen 825 serves the function of the liner, such as being sealed to a distal insulator and defining a lumen for the electrode array assembly. The tubing 801 can be made of an insulating polymer. In some examples, the tubing 801 can have an outer diameter of between about 0.030 inches (0.762 mm) and 0.165 inches (4.191 mm). The tubing 801 can be made from, for example, an extrusion of a polymer.

Tubing Having Wall Passages and Corrugations

Figure 9:
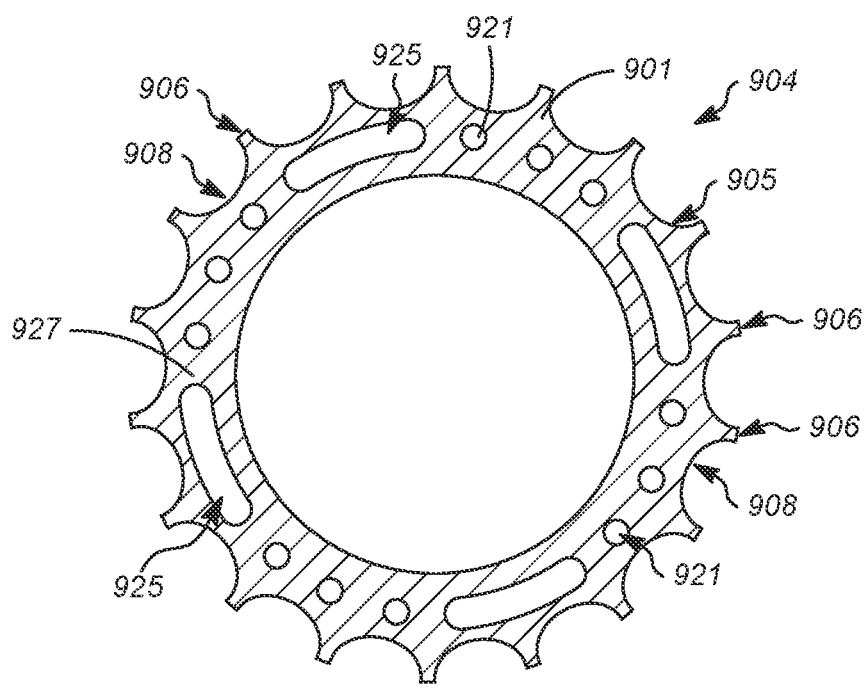
FIG. 9 is a cross-sectional view of an alternative tubing for a closed loop irrigation ablation probe according to some examples.

FIG. 9 is a cross-sectional view of an alternative tubing for a closed loop irrigation ablation probe according to some examples. In FIG. 9, the tubing 901 has a corrugated outer surface 905 with a plurality of corrugations 904 comprising a plurality of peaks 906 alternating with a plurality of troughs 908. The tubing 901 further has a plurality of passages 921, 925 in the wall 927 of the tubing 901. In the example of FIG. 9, twelve passages 921 have a circular cross-section and four passages 925 have an arced, elongate cross-section. The passages 921, 925 extend axially along the length of the tubing 901.

In one example, each of the passages 921, 925 provide inlet paths of the irrigation path and the outlet path is defined between an outer surface 905 of the tubing 901 and an inner surface of an outer sheath including an outer shaft electrode (not shown) surrounding the outside of the tubing 901. In some examples, two or more of the passages form portions of a first segment of a closed loop irrigation path. In some examples, two or more the passages 921, 925 form a portion of a second segment of the closed loop irrigation path.

The corrugations 904 can be provided in one of a number of different configurations. In some examples, the corrugations 904 extend along the length of the tubing 901 parallel to the axis of the ablation probe. In alternative examples, the corrugations 904 can be configured such that the peaks 906 and the troughs 908 wind helically around the outer circumference of the tubing 901. In some examples, and outlet path is formed between the outer surface 905 of the tubing 901 and an inner surface of an electrode (not shown) that is concentric around the outer surface 905 of the tubing 901. The corrugations 904 can direct the flow of cooling fluid in a direction diagonal to the axis of the ablation probe.

The tubing 901 can be made of an insulating polymer. In some examples, the tubing 901 can have an outer diameter of between about 0.020 inches (0.508 mm) and 0.0150 inches (0.3810 mm). The tubing 901 can be made from, for example, an extrusion of a polymer.

Temperature Sensors

Additional features contemplated for any of the ablation probes described herein include temperature sensors that can be incorporated in multiple locations on the probe, such as distal or proximal to the outer electrode. A thermocouple can be provided on the outer surface of the ablation probe to measure tissue temperature around the outer surface of the ablation probe. In addition or alternatively, a thermocouple can be provided near each edge of the outer electrode, such as spaced away from the electrode edge by about 1 mm. In addition or alternatively, a thin heat shrink material can be provided on top of a thermocouple in the system.

Radiofrequency Ablation Method

The various examples of radiofrequency ablation system as described herein can be used to perform a method of radiofrequency ablation. One example method of irrigated, bipolar radiofrequency ablation will now be described, where the ablation probe is positioned within the patient tissue to be ablated and the electrodes are electrically connected to the radiofrequency generator.

The method can be performed using a bipolar ablation probe that has a central channel and a distal opening. The probe has an outer sheath with a lumen and an outer electrode on the outer surface of the probe. An electrode array assembly disposed inside of the probe includes an electrode array for bipolar ablation. A tubing inside of the outer sheath partially defines a closed irrigation path that includes a first segment and a second segment. A coolant source is attached to the closed irrigation path.

The ablation probe is introduced into a patient so that the distal end of the ablation probe is positioned within tissue to be ablated. The method includes the steps of moving the electrode array assembly from a retracted configuration inside of the central channel of the ablation probe to a protruded configuration in which the electrode array protrudes from the distal opening of the probe. A pushrod of the electrode array assembly can be used to move the tines of the electrode array assembly from the retracted position within a shaft of the electrode array assembly and within the central channel of the ablation probe to a protruded configuration.

Either before or during ablation, closed loop irrigation is started. Fluid flow is provided through the closed irrigation path. In some examples of the closed loop irrigation path, the first segment is an inlet flow path that is nearer to the center of the tube than the second segment, which is an outflow path. In some examples, the flow rate of the fluid through the closed irrigation path can be between about 10 ml per minute and 90 ml per minute. In some examples, the flow rate can be between about 30 and 50 ml per minute. Different amounts of cooling fluid and different rates of irrigation could be used before or during the start of radiofrequency ablation.

The method further includes the step of attaching the electrode array and the outer electrode to a generator and providing radiofrequency current flow between the electrode array and the outer electrode. This step may occur before or after inserting the ablation probe into the patient. In some examples, radiofrequency ablation is started at 15 Watts while the closed loop irrigation continues. The power of the radiofrequency ablation is increased by 5 Watts every 30 seconds, as long as the tissue impedance decreases over the previous 30 seconds. An example of a minimum decrease required by this protocol is 3 Ohms. When the impedance decrease plateaus, which is likely to occur at about 25-30 Watts, then the power is increased by 2 Watts every 30 seconds. When impedance starts to increase, the power is no longer adjusted. The generator is allowed to adjust itself down in response to the increasing impedance according to its programming. After about 10 minutes, the radiofrequency ablation generator is stopped, although it may have shut itself down by that time according to its programming. For a larger lesion, the clinician can wait for 30 seconds and then restart this protocol at 50% of highest power used so far.

In a second round of the protocol for larger lesions, the power of the radiofrequency ablation is increased by 5 Watts every 30 seconds, as long as the tissue impedance decreases over the previous 30 seconds. When the impedance decrease plateaus, such as by decreasing by about 25-30 Watts every 30 seconds, then the power is increased by 2 Watts every 30 seconds. When impedance starts to increase, the power is no longer adjusted. The generator is allowed to adjust itself down in response to the increasing impedance according to its programming. After about 10 minutes, the radiofrequency ablation generator is stopped, although it may have shut itself down by that time according to its programming.

In various examples of bipolar radiofrequency ablation, such as that shown in FIGS. 1 and 2, the radiofrequency energy has a frequency of about 20 kHz to 5 MHz, or about 400 kHz to 500 kHz, for example 460 kHz. The target temperature for the embedded temperature sensor is between about 60° C. to 95° C., or about 80° C. The duration of radiofrequency energy application ranges from about 10 seconds to 5 minutes, or ranges from about 30 seconds to 2 minutes.

The outer electrode and the tines of the electrode array assembly can serve as the bipolar ablation electrodes. The radiofrequency energy can be applied (1) simultaneously, (2) sequentially or (3) in a time switching manner. A time switching manner means the energy is applied to one or more selected electrodes for a short period, such as 20 milliseconds, and then energy is applied to one or more other selected electrodes for another short period. The energy application switches quickly among electrodes.

After the desired ablation treatment, the electrode array assembly is moved into the retracted position. The ablation probe is removed from the patient.

Electrode Array Assembly Alternative as a Single Device with Ablation Probe

The various figures show examples that provide a liner with a central channel in which a separate electrode array assembly can be received and removed from. Other implementations are contemplated, and are within the scope of the disclosed technology, such as where the expandable electrode array is not a separate device, and the outer sheath and electrode array assembly are a single device. The electrode array assembly may be permanently positioned within the central lumen of the ablation probe, such as within the liner.

Wetting Agents for Inner Surface of Electrode

In any of the foregoing examples, the inner surface of the electrode can coated with a wetting agent to improve contact between the inner surface of the electrode and the cooling fluid, improving heat transfer between the electrode and the cooling fluid. Additionally, in some cases the polarity of the electrode can repel molecules of the cooling fluid of a different. A wetting agent can correct the polarity of the cooling fluid at the surface of the electrode to correct for this effect. Wetting agents can also correct surface effects created by textured surface elements on the inner surface of the electrode. For example, some wetting agents can prevent unwanted gas bubbles from forming on the surface of the electrode. Some examples of wetting agents that can be appropriate are sodium stearate, sodium lauroyl sarcosinate (INCI), perfluorononanoate, perfluorooctanoate (PFOA or PFO), alkylbenzene sulfonates lignin sulfonates, fatty alcohol ethoxylates, and alkylphenol ethoxylates. Fluorosurfactants, siloxane surfactant, polypropylene oxides, and many other classes of wetting agents can alternatively be used.

Textured Inner Surface of Electrode

In any of the foregoing examples, the electrode can have a textured inner surface that has peaks and troughs. The textured surface can increase the surface area of the inner surface of the electrode, allowing more cooling fluid to come in contact with the surface at any one time. In some examples, threading or knurling is used to create the texture. The knurled surface can include straight, angled, or cross-hatched grooves. Alternatively, the inner surface can be dimpled or ribbed to increase the cooing surface area. The inner surface of the outer sheath can also have a textured inner surface.

Electrode Leads

The electrode assemblies of the various examples of the technology are provided with electrically conductive leads to convey energy from a generator outside of the ablation catheter to the electrodes inside of a patient's body. The leads are configured to electrically connect the electrode elements of the electrode assembly to an external generator. The leads can be situated in a number of different configurations, based on the particular implementation of the ablation catheter. For example, the shaft of the electrode assembly can be constructed from an electrically conductive material, such as stainless steel, in which case the shaft can serve as the lead. In alternative examples, a wire positioned on the inner surface or the outer surface of the electrode assembly shaft can be used as a lead. In alternative examples, a lead can be placed within a wall of the electrode assembly, or the lead can be a conductive trace on the inner surface or the outer surface of the electrode assembly.

Each electrode assembly is provided with at least one lead. A separate lead can be provided for each electrode of an electrode assembly, so that individual electrodes can be held at different potentials.

Control of Axial Movement of Electrode Array Assembly

The electrode array assembly has an expanded configuration, a partially expanded configuration, and a retracted configuration in which the electrode array is unexpanded. In some examples, the expansion of the electrode array is continuously variable, meaning that the amount of protrusion of the individual tines can vary from completely retracted to completely expanded or any amount of expansion in between.

The electrode array assembly can include a push rod structure which is connected to the electrode arrays. The pushrod of the electrode array assembly is connected to the proximal end of the electrodes of the electrode array. The push rod receives a linear force from the user and in response moves the electrode array axially within a shaft of the electrode array assembly to protrude or retract the electrode tines from the distal of the shaft and the ablation probe. The pushrod of the electrode array assembly is slidably movable within the shaft of the electrode array assembly.

Electrode Elements and Electrode Arrays

While particular exemplary embodiments of electrode elements and electrode arrays are provided, the disclosure is not limited to the specific examples herein. Additional configurations are contemplated. In some examples, the electrode array is expandable from a first retracted position inside of the ablation catheter to an expanded position outside of the ablation catheter. In some examples, the electrode array comprises three or more electrode elements positioned at the distal end of the electrode assembly. In some examples, the electrode elements can be deployed selectively such that some electrode elements are in a retracted position at the same time that other electrode elements are in an expanded position. In some examples, multiple electrode elements are present and the distance between the electrode elements is adjustable.

The electrode tines of the electrode array assembly can be attached using a number of different constructions. For example, if the electrode assembly shaft is metal and the electrode tines are metal, the two can be welded together. In alternative arrangements, the electrode tines can be integrally constructed from the electrode assembly material, such as one when the electrode assembly shaft is a metal tube. In this example, the tube can be cut to the correct proportions to create the electrode elements. In alternative examples, the electrode elements can be attached using a collar or could be looped through openings at the end of the shaft.

Some of the figures are schematic in nature and are not drawn to scale. Certain features are shown larger than their scale and certain features are omitted from some views for ease of illustration.

It should be noted that, as used in this specification and the appended claims, the singular forms include the plural unless the context clearly dictates otherwise. It should also be noted that the term "or" is generally employed in its sense including "and/or" unless the content clearly dictates otherwise.

All publications and patent applications referenced in this specification are herein incorporated by reference in their entirety.

The disclosed technology has been described with reference to various specific and preferred embodiments and techniques. However, it should be understood that many variations and modifications may be made while remaining within the spirit and scope of the technology.

What is claimed is:

1. A closed loop irrigated ablation system comprising:
    an ablation probe defining a central channel with a distal opening, the ablation probe comprising:
        an outer sheath having a lumen, the outer sheath comprising an outer electrode;
        a tubing disposed in the lumen;
        a deployable electrode array assembly disposed inside an inner diameter of the tubing; and
        a closed irrigation path, the irrigation path having a first segment at least partially defined by the tubing and a second segment at least partially defined by an inner surface of the outer electrode; and
    a coolant source configured to deliver a cooling fluid to the closed irrigation path.

2. The system of claim 1 wherein the outer sheath comprises a conductive shaft partially covered by an insulator, wherein the outer electrode at least partially defines an outer surface of the ablation probe and at least partially defines the lumen, and wherein the outer electrode is an exposed axial section of the conductive shaft.

3. The system of claim 1 wherein the outer electrode is a ring electrode and the ablation probe comprises electrical leads connected to the ring electrode.

4. The system of claim 1 wherein the outer electrode comprises a textured inner surface.

5. The system of claim 1 wherein the inner surface of the outer electrode is coated with a wetting agent.

6. The system of claim 1 wherein the coolant source is configured to receive circulated cooling fluid from the closed irrigation path, and wherein the system is configured so that the first segment forms a portion of an inlet path for the cooling fluid moving toward a distal end of the ablation probe and configured so that the second segment forms a portion of an outlet path for the cooling fluid moving toward a proximal end of the ablation probe.

7. The system of claim 1 wherein the first segment and second segment of the irrigation path are concentric.

8. The system of claim 1 wherein the tubing is coaxial with the outer sheath, and wherein the tubing comprises an inner surface defining a tubing lumen and the first segment is defined by the inner surface of the tubing.

9. The system of claim 1 wherein the first segment is at least partially defined within a wall of the tubing, and wherein the second segment is at least partially defined between an outer surface of the tubing and the inner surface of the outer electrode.

10. The system of claim 9 wherein the wall of the tubing comprises at least four passages defining portions of the first segment.

11. The system of claim 1 wherein the tubing has a corrugated outer surface comprising corrugations.

12. The system of claim 1 wherein the tubing has an outer surface configured to direct the coolant to flow helically around the outer surface of the tubing.

13. The system of claim 1 wherein the tubing has a non-uniform thickness.

14. The system of claim 1 wherein the tubing is a polymer tube or an insulated stainless steel tube.

15. The system of claim 1 wherein the ablation probe further comprises a liner concentric with and within the tubing, wherein the first segment of the irrigation path is defined between the inner surface of the tubing and an outer surface of the liner.

16. The system of claim 15 wherein the liner defines the central channel of the ablation probe.

17. The system of claim 1 wherein the electrode array assembly comprises three or more electrode tines at a distal end of the electrode array assembly, and wherein the electrode array assembly has a retracted configuration where an electrode array is within the central channel of the ablation probe and a protruded configuration where the electrode array protrudes from the distal opening of the central channel.

18. A closed loop irrigated ablation system comprising:
    an ablation probe defining a central channel with a distal opening, the ablation probe comprising:
        an outer sheath having a lumen, the outer sheath comprising a conductive shaft partially covered by an insulator, wherein an exposed portion of the conductive shaft forms an outer electrode;
        a tubing disposed in the lumen;

a liner concentric with and within the tubing;

a deployable electrode array assembly disposed inside an inner surface of the liner; and a closed irrigation path, the irrigation path having a first segment at least partially defined by an inner surface of the tubing and the outer surface of the liner and a second segment at least partially defined by an inner surface of the outer electrode; and a coolant source configured to deliver a cooling fluid to the closed irrigation path.

19. A radiofrequency ablation method comprising:

providing an ablation probe defining a central channel with a distal opening, the ablation probe comprising:

an outer sheath having a lumen, the outer sheath comprising an outer electrode, a tubing disposed in the lumen;

an electrode array assembly disposed inside an inner diameter of the tubing, and a closed irrigation path, the irrigation path having a first segment at least partially defined by the tubing and a second segment at least partially defined by an inner surface of the outer electrode;

moving the electrode array assembly between a retracted configuration where an electrode array is within the central channel of the ablation probe and a protruded configuration where the electrode array protrudes from the distal opening of the central channel;

attaching a coolant source to the closed irrigation path;

providing fluid flow through the closed irrigation path; and attaching the electrode array and outer electrode to a generator and providing radiofrequency current flow between the electrode array and the outer electrode.

20. The method of claim 19 wherein providing fluid flow through the closed irrigation path comprises providing a helical fluid flow around an outer surface of the tubing.

* * * * *